United States Patent [19]

Ehmann et al.

[11] 4,298,762

[45] * Nov. 3, 1981

[54] PROCESS FOR THE OXIDATION OF PRIMARY ALLYLIC AND BENZYLIC ALCOHOLS

[75] Inventors: William J. Ehmann, Orange Park; Walter E. Johnson, Jr., Jacksonville, both of Fla.

[73] Assignee: SCM Corporation, New York, N.Y.

[*] Notice: The portion of the term of this patent subsequent to Oct. 25, 1994, has been disclaimed.

[21] Appl. No.: 100,558

[22] Filed: Dec. 5, 1979

Related U.S. Application Data

[63] Continuation of Ser. No. 582,113, May 30, 1975, abandoned.

[51] Int. Cl.$^3$ ............................................. C07C 45/29
[52] U.S. Cl. .................................. 568/433; 568/460; 568/445; 568/446; 260/347.8
[58] Field of Search .................. 260/603 C, 599, 596; 568/433, 460, 465, 445, 446

[56] References Cited

U.S. PATENT DOCUMENTS 2,801,266  7/1957  Schinz ................................. 260/587
4,055,601 10/1977  Ehmann ....................... 260/603 C X

OTHER PUBLICATIONS

Djerassi (I), Organic Reactions, vol. VI (1951), pp. 222–224, 266–267, 208–209.
Adkins et al., J.A.C.S., vol. 71 (1949), pp. 3622–3629.
Batty et al., Chemical Society (London) Journal (1938), pp. 175–179.
Rekasheva et al., Chemical Abstracts, vol. 46 (1952) 1965(d).
Wilds, Organic Reactions, vol. II (1944), pp. 178–179.

*Primary Examiner*—Bernard Helfin
*Attorney, Agent, or Firm*—Richard H. Thomas; Merton H. Douthitt

[57] ABSTRACT

Improved conversions of primary allylic and benzylic alcohols are obtained in an Oppenauer oxidation process, under Oppenauer oxidation conditions, by carrying out the oxidation employing furfural as the hydrogen acceptor. Primary alcohols to which the present invention relates are allylic alcohols substituted in at least the 2-position with a hydrocarbon radical and benzylic alcohols.

7 Claims, No Drawings

PROCESS FOR THE OXIDATION OF PRIMARY ALLYLIC AND BENZYLIC ALCOHOLS

This is a continuation of application Ser. No. 582,113, filed May 30, 1975 and now abandoned.

BACKGROUND OF THE INVENTION

The present invention relates to the Oppenauer oxidation of primary alcohols to their corresponding aldehydes. The invention is particularly applicable to the oxidation of primary allylic alcohols substituted in at least the 2-position with a hydrocarbon radical and primary benzylic alcohols. The allylic double bond may be acyclic, exocyclic or endocyclic.

An example of a cyclic allylic alcohol to which the present invention relates is perillyl alcohol (1-hydroxymethyl-4-isopropenylcyclohexene). An example of a benzylic alcohol to which the present invention relates is benzyl alcohol.

The present application is related to co-pending application Ser. No. 437,188, filed Jan. 28, 1974, now abandoned, and also to the continuation-in-part application thereof, executed concurrently herewith, Ser. No. 582,114 and now U.S. Pat. No. 4,055,601, both said applications being assigned to assignee of the present application. The inventions of said co-pending applications reside in the Oppenauer oxidation of 3-substituted and 3,3-disubstituted alcohols, such as geraniol and nerol (3,7-dimethyl-2,6-octidien-1-ol), to the corresponding aldehydes, such as citral. The disclosure of said co-pending applications are incorporated by reference herein.

DESCRIPTION OF THE PRIOR ART

The Oppenauer oxidation of secondary alcohols to ketones is a useful and well-known textbook reaction. The oxidation is carried out generally in the presence of an aluminum catalyst such as aluminum tert-butoxide or aluminum isopropoxide employing a large excess of acetone as a hydrogen acceptor. The general application of this reaction is, however, for secondary alcohols. It is reported in *Organic Reactions*, Vol. VI, chapter 5, on "The Oppenauer Oxidation" (pages 222-223) by Carl Djerassi, John Wiley and Sons Inc., 1951; "Until very recently the Oppenauer reaction, except in isolated instances, has not been used as a preparative method for the oxidation of primary alcohols to aldehydes because the aldehydes condensed with the hydrogen acceptor." As indicated by Djerassi, experimental modifications in the usual Oppenauer procedure are necessary. These include the use of expensive or difficult to come by hydrogen acceptors, use of stoichiometric amounts of catalyst and careful distillation of the product as it is formed. The methods are expensive, difficult to carry out on a large scale and are employed only when no other method is available.

The Djerassi text in *Organic Reactions* is incorporated by reference herein.

Previous observations of the oxidation of primary alcohols such as geraniol and nerol with acetone as a hydrogen acceptor show that the aldehydes produced undergo a subsequent aldol condensation reaction with the acetone and little aldehyde (citral) is actually recoverable. Although the end product of the aldol condensation of citral is pseudoionone, two major problems have kept this reaction from being employed in the production of pseudoionone commercially. One problem is that the aldol condensation reaction produces water as a by-product which hydrolyzes and consumes the aluminum catalyst. This requires nearly stoichiometric quantities (as compared to catalytic quantities) of the aluminum catalyst (notice page 224 of Djerassi, supra). In addition, the hydrolyzed catalyst is in the form of a gel-like precipitate which is difficult to dispose of and which also presents mechanical problems in carrying out the oxidation reaction. Still further, large amounts of solvent are required to dissolve the correspondingly large amount of catalyst employed for the oxidation reaction. A second disadvantage is that if the reaction is carried to high conversion, the yield tends to fall off.

Substituting hydrogen acceptors such as cyclohexanone, which are less likely to undergo an aldol condensation, for the acetone may improve the aldehyde yield. Still, relatively high reaction temperatures are required when using ketones as hydrogen acceptors to carry out the oxidation to high conversion in a reasonable time. High temperatures would be a disadvantage with heat-sensitive aldehydes such as citral, as these are capable of self-condensation at high temperatures. In addition, other ketonic hydrogen acceptors present problems of availability or low equilibrium constants, the latter necessitating a large excess of hydrogen acceptor which causes difficulty in subsequent isolation of products.

Djerassi on page 230 points out: "Until recently aldehydes have been used only infrequently as hydrogen acceptors." Aldehydes are traditionally difficult products to make, being unstable and subject to side reactions. Use of an aldehyde as a reactant or hydrogen acceptor is subject to the same problems, being equally unstable and subject to side reactions. In the Oppenauer oxidation process, it is likely to undergo both aldol and Tischenko condensation reactions, with both itself and with the Oppenauer oxidation product.

A number of studies have been conducted by Adkins and others (for instance, Adkins et al, *J. Am. Chem. Soc.*, Vol. 71, pages 3622-3629) to determine the apparent oxidation potentials of various compounds (primarily ketones). Although it can be concluded that a high oxidation potential is desirable, a relatively low one (as pointed out by Djerassi on page 228) can be offset by using a large excess of hydrogen acceptor, and other factors such as rate of reaction and potential for side reactions may be more controlling. For instance, acetone has a relatively low oxidation potential but is inexpensive and can be used in large excess. Cyclohexanone on the other hand has a higher oxidation potential, but in comparative tests conducted with this compound, the oxidation of geraniol resulted in only 15% conversion to citral.

SUMMARY OF THE INVENTION

The present invention resides in the discovery that furfural unexpectedly constitutes a superior oxidizing agent or hydrogen acceptor for the conversion of primary allylic and benzylic alcohols to their corresponding aldehydes. Primary allylic alcohols to which the present invention relates are; allylic alcohols substituted in at least the 2-position with a hydrocarbon radical; the allylic double bond may be acyclic exocyclicor endocyclic and the 3-position may be unsubstituted, monosubstituted or disubstituted. The reaction of the present invention is carried out under mild Oppenauer oxidation conditions in the presence of an aluminum catalyst. By way of example, the reaction can be represented by the following equation, employing perillyl alcohol as a substrate:

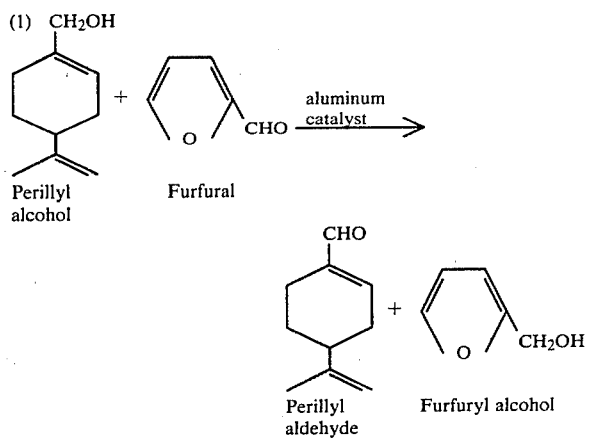

(1) Perillyl alcohol + Furfural —aluminum catalyst→ Perillyl aldehyde + Furfuryl alcohol Under the mild reaction conditions, it was discovered that furfural does not undergo a Tischenko reaction as is common with many aldehydes. Moreover, furfural, having no alpha-protons, does not undergo an aldol condensation with the aldehyde product, for instance perillyl aldehyde, as does acetone. Hence, the amount of aluminum catalyst required for the reaction is greatly reduced to catalytic quantities, eliminating the attendant mechanical and pollution problems, and reducing catalyst cost.

Surprisingly the reaction of furfural with primary allylic alcohols such as perillyl alcohol, and also with primary benzylic alcohols, has a high rate of reaction which permits it to be carried out under very mild conditions. This is important for heat-sensitive or highly reactive compounds. Specifically, at the mild conditions of the reaction of the present invention, perillyl aldehyde, itself, undergoes no aldol self-condensation. Also, at the mild conditions of the present invention, no appreciable side reactions occur.

The reaction of the present invention also has a fortuitous high equilibrium constant so that it results in high conversion and yields of the aldehyde without employing a large excess of furfural.

Preferably, the reaction of furfural and alcohol is carried out with a molar ratio of furfural to alcohol of about 1:10 to about 10:1. A preferred range is about 1:2 to about 3:1 which results in high yields of the desired products without excessive amounts of unreacted starting materials. The specific ratio selected, however, depends on the end products desired.

Preferably, a catalytic amount of about 1-15 mol % (based on the weight of primary allylic alcohol charged) of an aluminum catalyst such as aluminum isopropoxide is employed, although this depends in part on the amount of water present in the reaction mixture.

The use of less than 2 mol % catalyst is possible if extreme care is taken with regard to the water content. Other factors dictating the amount of catalyst employed include rate of reaction desired, amount of coincidental acid present in the reaction mixture, and the amount of water or acid produced in the course of the reaction.

Any aluminum alkoxide or aluminum aryloxide catalyst useful in an Oppenauer reaction, such as aluminum tert-butoxide [Al(t-OC$_4$H$_9$)$_3$], may be used. Aluminum isopropoxide is preferred as it offers a cost advantage and an advantage in availability, although some furfural is consumed by oxidation of the isopropoxide to acetone. In this regard, it is reported in the aforementioned *Organic Reactions*, Vol. VI, page 209 (Djerassi) and also in *Physical Organic Chemistry*, by Hine, that the true active catalyst in the oxidation is an aluminum alkoxide which is generated in situ, and thus is dependent upon the reactants and conditions. It is normally generated by the addition of aluminum isopropoxide, aluminum t-butoxide or aluminum phenoxide. It may also be generated in situ by addition of an alkyl aluminum compound such as triisobutylaluminum (Djerassi also lists a number of other suitable compounds). These compounds, although they are normally referred to as the catalyst, are merely the source of the aluminum alkoxide. Hence the choice of aluminum source is largely one of convenience. For the purpose of this application, the term "Oppenauer Oxidation Catalyst" shall be deemed to embrace all of the above compounds.

Representative alcohols to which the present application is directed are set forth in the following Table 1:

TABLE 1

| Structure | Name |
|---|---|
| CH$_2$=C(CH$_3$)—CH$_2$OH | Methallyl alcohol |
| (cyclohexene with CH$_2$OH and isopropenyl substituents) | Perillyl alcohol |
| C$_6$H$_5$—CH$_2$OH | Benzyl alcohol |

It is apparent that the above alcohols have in common a hydrocarbon substitution at the 2-position beta to the carbinol hydroxy radical. They may or may not be substituted in the 3-position, and the substitution can be by any aliphatic or aromatic radical. Other representative benzylic alcohols within the scope of the present invention are such polyhydroxyl compounds as saligenin [o-HOC$_6$H$_4$CH$_2$OH], para hydroxy benzyl alcohol [p-HOC$_6$H$_4$CH$_2$OH], and vanillyl alcohol [α, 4-dihydroxy-3-methoxytoluene]. For purposes of the present application, the term "benzylic alcohol" has the common meaning that it defines hydroxy methyl aromatic compounds.

An example of another cyclic allylic alcohol in which the allylic double bond is endocyclic is myrtenol:

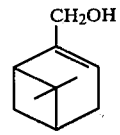

Other primary alcohols within the scope of the present invention will be apparent to those skilled in the art.

The following examples illustrate the present invention and its practice, but should not be considered as limiting it. In this specification, all percentages are by weight, all parts are parts by weight, and all temperatures are in degrees Centigrade unless otherwise specified.

EXAMPLE 1

This example illustrates the oxidation of perillyl alcohol to perillyl aldehyde.

A flask was charged with 100 ml. of toluene and 160 grams of furfural and heated to reflux to remove any water present by azeotropic distillation. The solution was then cooled to room temperature and 50 grams of perillyl alcohol and 2.5 grams of aluminum isopropoxide were added. The solution was then heated to 75° C. for three hours. Analysis by glpc showed over 90% conversion to perillyl aldehyde.

EXAMPLE 2

This example illustrates the principles of the invention in the Oppenauer oxidation of benzyl alcohol to benzaldehyde. A flask equipped with a Dean-Stark trap was charged with 32.5 grams (0.3 mol) of benzyl alcohol and 30 ml of toluene and heated to reflux to remove any water present by azeotropic distillation. The solution was cooled to room temperature and 28.8 grams (0.3 mol) of furfural and 2.0 grams (0.01 mol) of aluminum isopropoxide were added. The mixture was stirred at ambient temperature and sampled periodically for analysis by glpc. After 5 hours 61.5% of the benzyl alcohol was converted to benzaldehyde and 68.3% of furfural was converted to furfuryl alcohol.

After 72 hours, conversion to benzaldehyde increased to 63.9% and conversion to furfuryl alcohol increased to 74.5%. No by-products derived from either benzyl alcohol or furfural were detected by glpc.

EXAMPLE 3

A flask was charged with 3.1 grams (20 mmol) of 2,6-dimethyl-2,7-octadien-1-ol, 0.3 grams (1.5 mmol) of aluminum isopropoxide, and 2.0 grams (21 mmol) of furfural, and stirred 16 hours at ambient temperature. Analysis of the product by vapor phase chromatography showed 95% conversion of the starting alcohol to 2,6-dimethyl-2,7-octadienal.

What is claimed is:

1. An Oppenauer oxidation of a primary alcohol selected from the group consisting of; methallyl alcohol, perillyl alcohol, myrtenol, benzyl alcohol, p-hydroxy benzyl alcohol, saligenin, vanillyl alcohol and 2,6-dimethyl-2,7-octadien-1-ol to the corresponding aldehyde in the presence of from 1 to 15 mol percent based on the alcohol charged of an Oppenauer oxidation catalyst and furfural as the hydrogen acceptor under mild temperature Oppenauer oxidation conditions said temperature being in the range of from ambient temperature to 75° C., said hydrogen acceptor being present in a molar ratio of furfural to primary alcohol of about 10:1–1:10, and forming a reaction product mixture containing the aldehyde corresponding to the primary alcohol, and as a by-product, furfuryl alcohol.

2. The oxidation process of claim 1 wherein said Oppenauer reaction is carried out with a molar ratio of furfural to primary alcohol in the range of 3:1 to 1:2.

3. The oxidation process of claim 1 wherein the primary alcohol is perillyl alcohol (1-hydroxymethyl-4-isopropenylcyclohexane).

4. The oxidation process of claim 1 wherein said primary alcohol is benzyl alcohol.

5. The oxidation process of claim 1 wherein said alcohol is methallyl alcohol.

6. The oxidation process of claim 1 wherein said alcohol is 2,6-dimethyl-2,7-octadien-1-ol.

7. The oxidation process of claim 1 wherein said alcohol is myrtenol.

* * * * *

UNITED STATES PATENT AND TRADEMARK OFFICE
CERTIFICATE OF CORRECTION

PATENT NO. : 4,298,762
DATED : November 3, 1981
INVENTOR(S) : William J. Ehmann and Walter E. Johnson It is certified that error appears in the above-identified patent and that said Letters Patent are hereby corrected as shown below:

Column 2, line 64, change "acyclic exocyclicor" to read --acyclic, exocyclic, or--. Column 6, line 27, change "isopropenylcyclohexane)." to --isopropenylcyclohexene).--.

Signed and Sealed this

Twenty-sixth Day of January 1982

[SEAL]

*Attest:*

*Attesting Officer*

GERALD J. MOSSINGHOFF
*Commissioner of Patents and Trademarks*